(12) United States Patent
Chen et al.

(10) Patent No.: US 7,316,766 B2
(45) Date of Patent: Jan. 8, 2008

(54) ELECTROCHEMICAL BIOSENSOR STRIP

(75) Inventors: Chun-Tung Chen, Taipei (TW); Tsai-Yun Lee, Sindian (TW); Shu-Mei Wu, Taipei (TW); Chia-Chi Wu, Kaohsiung (TW); Chun-Hui Pi, Yonghe (TW); Chao-Wang Chen, Taipei (TW)

(73) Assignee: Taidoc Technology Corporation, Taipei (TW)

( * ) Notice: Subject to any disclaimer, the term of this patent is extended or adjusted under 35 U.S.C. 154(b) by 314 days.

(21) Appl. No.: 11/138,403

(22) Filed: May 27, 2005

(65) Prior Publication Data
US 2006/0266645 A1    Nov. 30, 2006

(51) Int. Cl.
*G01N 27/327* (2006.01)

(52) U.S. Cl. .................. 204/403.01; 204/403.02; 204/403.14

(58) Field of Classification Search ........... 205/777.5, 205/778, 792; 204/403.01–403.15
See application file for complete search history.

(56) References Cited

U.S. PATENT DOCUMENTS

| | | | |
|---|---|---|---|
| 6,451,372 B2 * | 9/2002 | Hasegawa et al. | 427/2.13 |
| 6,814,843 B1 * | 11/2004 | Bhullar et al. | 204/403.01 |
| 6,827,829 B2 * | 12/2004 | Kawanaka et al. | 204/403.02 |
| 6,942,770 B2 * | 9/2005 | Cai et al. | 204/403.04 |
| 2004/0178067 A1 * | 9/2004 | Miyazaki et al. | 204/403.01 |

FOREIGN PATENT DOCUMENTS

JP    2004-4017 A    *    1/2004

OTHER PUBLICATIONS

JPO English language translation of Shuzo et al. (JP 2004-004017 A).*

* cited by examiner

*Primary Examiner*—Alex Noguerola

(57) ABSTRACT

An electrochemical biosensor strip has a base, an electrode system, an optional spacer and a cover. The electrode system is laid on the base. The spacer is laid on the electrode system and exposes a portion of the electrode system for electrical connection with a meter and a different portion of the electrode system for application of a test reagent. The cover is covered on the spacer to form a cavity. Between the test reagent and the base, a hydrophilic layer is laid between them for increasing the binding effect of the test reagent on the base. The hydrophilic layer is laid on the area excluding from the electrode system and laid on the electrode system about 50% to 0% of the electrode system corresponding to the test reagent. The hydrophilic layer will not interfere with signal transmission of the electrode system so the test is more accurate.

19 Claims, 6 Drawing Sheets

ELECTROCHEMICAL BIOSENSOR STRIP

BACKGROUND OF THE INVENTION

1. Field of the Invention

The present invention relates in general to an electrochemical biosensor strip. More particularly, the present invention relates to an electrochemical biosensor strip that has a hydrophilic layer laid under a test reagent and excluded from an electrode system corresponding to the test reagent for increasing the test reagent binding on a base and preventing the hydrophilic layer interfering with signal transmission.

2. Description of the Related Art

Since the improvement of the science and technology, many tests can be operated by users in house. In the market, many disposable strips are used for measuring specific components in a biological fluid and can be operated by users in house. Analytical biosensor strips are useful in chemistry and medicine to determine the presence and concentration of a biological analyte. Such strips are needed, for example, to monitor glucose in diabetic patients and lactate during critical care events. Biosensor strips are used in the chemical industry, for example, to analyze complex mixtures. They are also used in the food industry and in the biochemical engineering industry. Biosensor strips are also useful in medical research or in external testing. In external testing, they can function in a non-invasive manner (i.e., where they come into contact with blood withdrawn by a syringe or a pricking device).

Conventional electrochemical biosensor strip has a base, an electrode system, an insulating substrate, a test reagent and a cover. The electrode system is laid on the base and comprises two electrodes separated from each other. The insulating substrate is laid down onto the electrode system and has a first opening and a second opening. The first opening exposes portions of the electrode system for electrical connection with a meter, which measures some electrical property of a test sample after the test sample is mixed with the test reagent of the strip. The second opening exposes a different portion of the electrode system for application of the test reagent to those exposed surfaces of electrode system. The test reagent is a reagent that is specific for the test to be performed by the strip. The test reagent may be applied to the entire exposed surface area of the electrode system in the area defined by the second opening. The cover is covered on the electrode system and the test reagent for protecting the test reagent.

However, since the base is prepared by polyethylene terephthalate (PET) or polyvinyl chloride (PVC) which is hydrophobic, the test reagent laid on the base is unstable. The strip is manufactured by a sheet of the PET or PVC substance and the sheet is cut for forming multiple strips after every needed substances are laid on the sheet. When the cutting step is proceeding, the test reagent is easy to shake off from the base. Besides, the electrode locates on the base so as to protrude from the base such that a surface that the test reagent layer laid on is not a flat plane. It will cause the test reagent spread on the base unequally so as to interfere with the detecting result.

SUMMARY OF THE INVENTION

One aspect of the present invention is to provide an electrochemical biosensor strip which has a hydrophilic layer for increasing a test reagent layer bond on a base strongly and which dose not locate corresponding to an electrode system for avoiding from interfering with signal transmission so as to increase test accuracy.

Accordingly, the electrochemical biosensor strip of the present invention comprises a base, an electrode system, a hydrophilic layer, a test reagent and a cover. The electrode system is laid on the base and a portion of the electrode system is utilized for electrical connection with a mating meter, which measures some electrical property of an analyte-containing fluid after an analyte-containing fluid is mixed with the test reagent of the strip. A predetermined portion of the electrode system is applied for the test reagent to those exposed surfaces of electrode system. The test reagent is a reagent that is specific for the test to be performed by the strip. The test reagent may be applied to the entire exposed surface area of the electrode system. The cover locates on a top and mated with the base for providing a cavity so as to draw the analyte-containing fluid into the electrochemical biosensor strip by capillary phenomenon. Under the test reagent, the hydrophilic layer is laid between the test reagent and the base and laid on the base corresponding to the cavity and excluding from the electrode system and laid on the electrode system about 50% to 0% of the electrode system corresponding to the test reagent. The hydrophilic layer will let the test reagent bond strongly and equally on the base and prevent from interfering with signal transmission of the electrode system, and therefore, the test is more accuracy.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
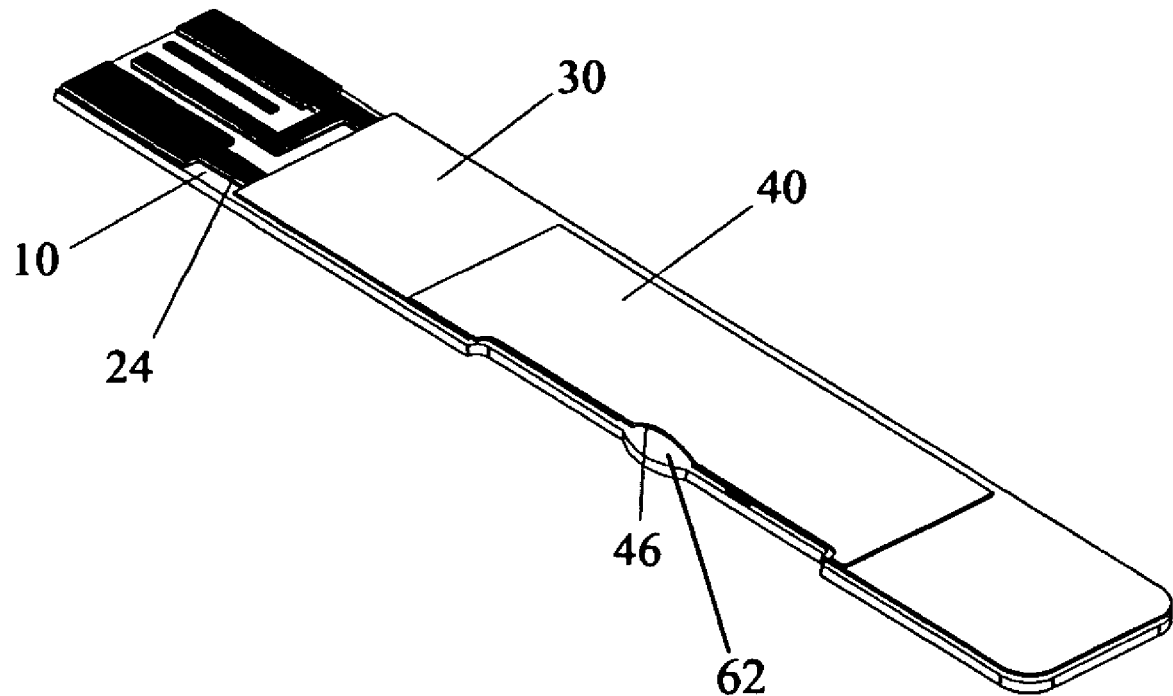
FIG. 1 is a perspective view of a first embodiment of an electrochemical biosensor strip in accordance with the present invention.
Figure 2:
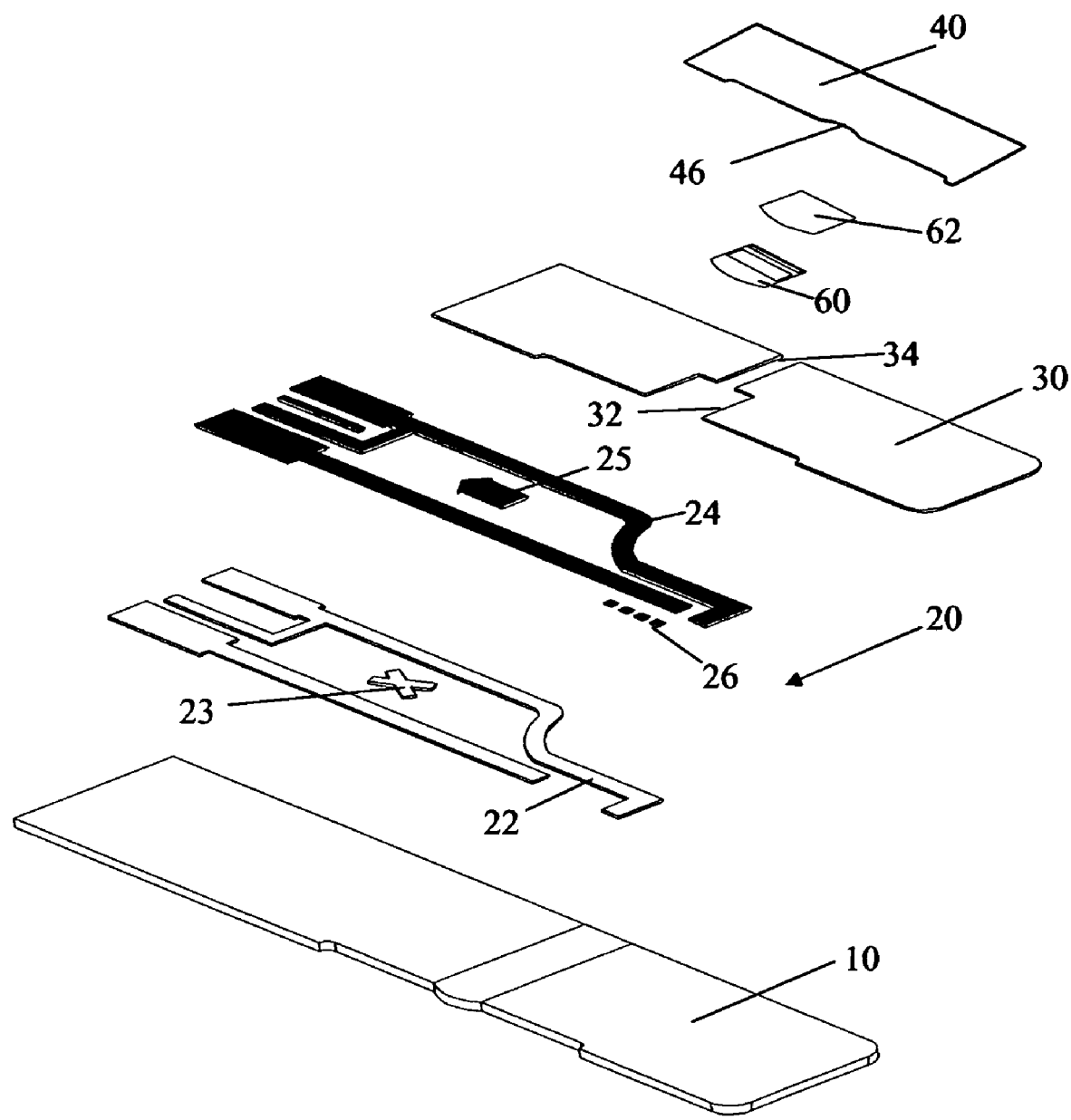
FIG. 2 is an exploded perspective view of the electrochemical biosensor strip in FIG. 1.

With reference to FIGS. 1 and 2, a first embodiment of an electrochemical biosensor strip in accordance with the present invention comprises a base (10), an electrode system (20), a spacer (30), a hydrophilic layer (60), a test reagent (62) and a cover (40).

The base (10) may be rectangular and preferably is an insulating substance. The electrode system (20) is laid on the base (10) and preferably comprises two layers that are a silver layer (22) and a carbon layer (24). The silver layer (22) is laid on the base (10) and the carbon layer (24) is laid on the silver layer (22). The carbon layer (24) and the silver layer (22) respectively comprise at least three electrodes that respectively have a first end and a second end. In the drawings, the silver layer (22) has three electrodes and the carbon layer (24) has four electrodes. There is a short circuit formed between two electrodes of the carbon layer (24) and the corresponding electrodes of the silver layer (22). Other electrodes are separated so that the electrodes do not interfere with the electrochemical events at the other electrode. Preferably, one electrode of the electrodes that formed the short circuit is a reference electrode. The short circuit is utilized to switch on a mating meter. There is at least one working electrode included in the electrode system (20).

The first ends of the electrodes are parallel and formed along a long edge of the strip. The second ends of the electrodes are defined corresponding to the test reagent (62). Preferably, the silver layer (22) further has a forked shape unit (23) formed between the electrodes. More preferably, the carbon layer (24) further has an arrowhead shape unit (25) formed on the forked shape unit (23) of the silver layer (22). When users are inserting wrong direction of the strip, the users will see the forked shape unit (23) for reminding the users that the direction is wrong. On the contrary, the users will see the arrowhead shape unit (25) when the inserting direction is correct.

The biosensor strip further has a rough unit (26) laid on the base (10) and located corresponding to the test reagent (62). Preferably, the rough unit (26) is a line or multiple lines and more preferably laid on an outside of the second end of the electrodes and adjacent to the electrodes. The rough unit (26) is preferably prepared by electric conduction substance or non-electric conduction substance. More preferably, the rough unit (26) is prepared by carbon and separated from the electrode system (20). For decreasing manufacturing cost, the rough unit (26) is printed by carbon when the carbon layer (24) of the electrode system (20) is printing. The rough unit (26) can increase the rough of the base (10), and therefore, the test reagent (62) laid on the base (10) will not easy to be shaking off when the strip is cut for separating. In addition, the rough unit (26) is located on the outside of the electrode system (20) so the rough unit (26) can form a wall for protecting the test reagent (62) from falling.

The spacer (30) is laid on the electrode system (20) and comprises an opening (32) and an exhausting channel (34). The electrodes will be exposed when the spacer (30) is laid on the electrode system (20) for electrical connection with a mating meter which measures some electrical property of an analyte containing fluid after the analyte-containing fluid is mixed with the test reagent (62) of the strip. The opening (32) exposes a predetermined portion of the electrode system (20) for application of the test reagent (62) to the exposed surface of electrode system (20). The opening (32) is preferably formed in a side of the spacer (30). The exhausting channel (34) is communicates with the opening (32) for exiting air and preferably the exhausting channel (34) formed extendedly from the opening (32) and opened to another side. Therefore, the exhausting channel (34) is used to increase the flow rate of an analyte-containing fluid drawn in the opening (32) such that the reaction is almost equal so as to increase the accuracy.

The hydrophilic layer (60) is laid on the base (10) corresponding to the opening (32). Preferably, the hydrophilic layer (60) is laid on an area of the base (10) corresponding to the opening (32) and excluding from the electrode system (20) and laid on the electrode system (20) about 50% to 0% of the electrode system (20) corresponding to the opening (32). More preferably, the hydrophilic layer (60) is laid on the area of the base (10) corresponding to the opening (32) and excluding from the electrode system (20). On another aspect, the hydrophilic layer (60) laid on the area of the base (10) corresponding to the opening (32) and excluding from the working electrode and laid on the working electrode about 50% to 0% of the working electrode corresponding to the opening (32). Preferably, the hydrophilic layer (60) is laid on the area of the base (10) corresponding to the opening (32) and excluding from the working electrode. Furthermore, the hydrophilic layer (60) is at least one strip-like shape formed on the working electrode for increasing the effect of the test reagent (62) spreading on the working electrode and making the distribution of the test reagent (62) lay on the hydrophilic layer (60) equally. The hydrophilic layer (60) is a plurality of strip-like shape formed on the base (10) corresponding to the opening (32) excluding from the working electrode. The hydrophilic layer (60) preferably is composed of hydrophilic substances, and more preferably, the hydrophilic layer (60) is composed of soluble cellulose. The hydrophilic layer (60) may be composed of methylcellulose (MC), carboxymethyl cellulose (CMC), methylhydroxyethylcellulose (MHEC), methylhydroxypropylcellulose (MHEC), methylhydroxypropylcellulose (MHPC), hydroxyethylcellulose (HEC), hydroxyethylcarboxymethylcellulose (HECMC), carboxymethylhydroxyethylcellulose (CMHEC) or a combination thereof. In addition, the hydrophilic layer (60) may be composed of surfactant, strengthening of viscosity agent, organic polar compound or a combination thereof. Preferably, the organic polar compound has a boiling point at 200° C. to 300° C.

Figure 3A:
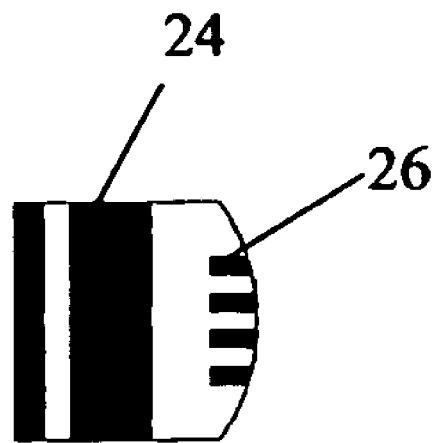
FIG. 3A is a plan view of an area of a base corresponding to an opening of a spacer of the electrochemical biosensor strip in FIG. 1 showing a distribution of an electrode system and a rough unit corresponding to the opening of the spacer without laying a hydrophilic layer and a test reagent.
Figure 3B:
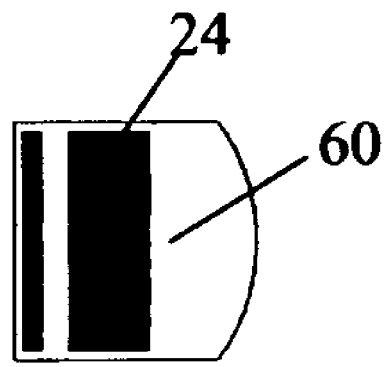
FIG. 3B is a plan view of the area in FIG. 3A showing the hydrophilic layer laid on the area without laying the test reagent.

With further reference to FIG. 3A, it is an enlarging figure showing a portion of the base (10) corresponding to the opening (32) of the spacer (30) which provides the distribution of the electrode system (20) and the rough unit (26) on the base (10). It is not covered with the hydrophilic layer (60). With further reference to FIG. 3B, the hydrophilic layer (60) is covered on the base (10) corresponding to the opening (32) of the spacer (30) which is laid on the area excluding from the electrode system (20) and laid on the electrode system (20) about 50% to 0% of the electrode system (20) corresponding to the test reagent (62). The hydrophilic layer (60) may be covered on the base (10) by printing, evaporation or spotting etc.

The test reagent (62) is a reagent that is specific for the test to be performed by the strip. The test reagent (62) may be applied to the entire exposed surface area of the electrode system (20) in the area defined by the opening (32). The cover (40) is covered on the spacer (30) to protect the test reagent (62) and preferably together with the opening (32) to form a cavity. When an analyte-containing fluid, for example, a drop of blood, has been drawn in the opening (32) of the strip, the analyte reacts with the test reagent (62) and an output signal corresponding to a sensing current is generated and is detected by a mating meter. Preferably, the spacer (30) may be not needed and the cover (40) is cooperated with the base (10) to form a cavity for drawing the analyte-containing fluid by capillary phenomenon. The cover (40) has a concave unit (46) that is formed corresponding to the opening (32) of the spacer (30) to help the analyte-containing fluid drawn into the opening (32) of the spacer (30) and increase variety angles for drawing the fluid. Preferably, the concave unit (46) is semicircle-shape or semi-ellipse-shape.

Since the base (10) is manufactured by hydrophobic substances, the test reagent (62) is not easy to bind on the base (10) strongly. The electrochemical biosensor strip in accordance with the present invention provides a hydrophilic layer (60) laid on the base before the test reagent (62) laid on the base (10). The hydrophilic layer (60) will let the base (10) favorite for binding the test reagent (62) so as to increase the effect of the test regent (62) spreading on the base (10) and make the test reagent (62) distribute equally. Besides, if the hydrophilic layer (60) is laid on the electrode system (20) not equally (20), the signal transmission of the electrode system (20) will decay and let the distribution of the test reagent (62) not equally. Since the hydrophilic layer (60) will interfere with signal transmission, the hydrophilic layer (60) must exclude from the electrode system (20). Therefore, the hydrophilic layer (60) laid on the area exception from the electrode system (20) corresponding to the test reagent (62) and laid on the electrode system (20) about 50% to 0% of the electrode system (20) corresponding to the test reagent (62).

Figure 4:
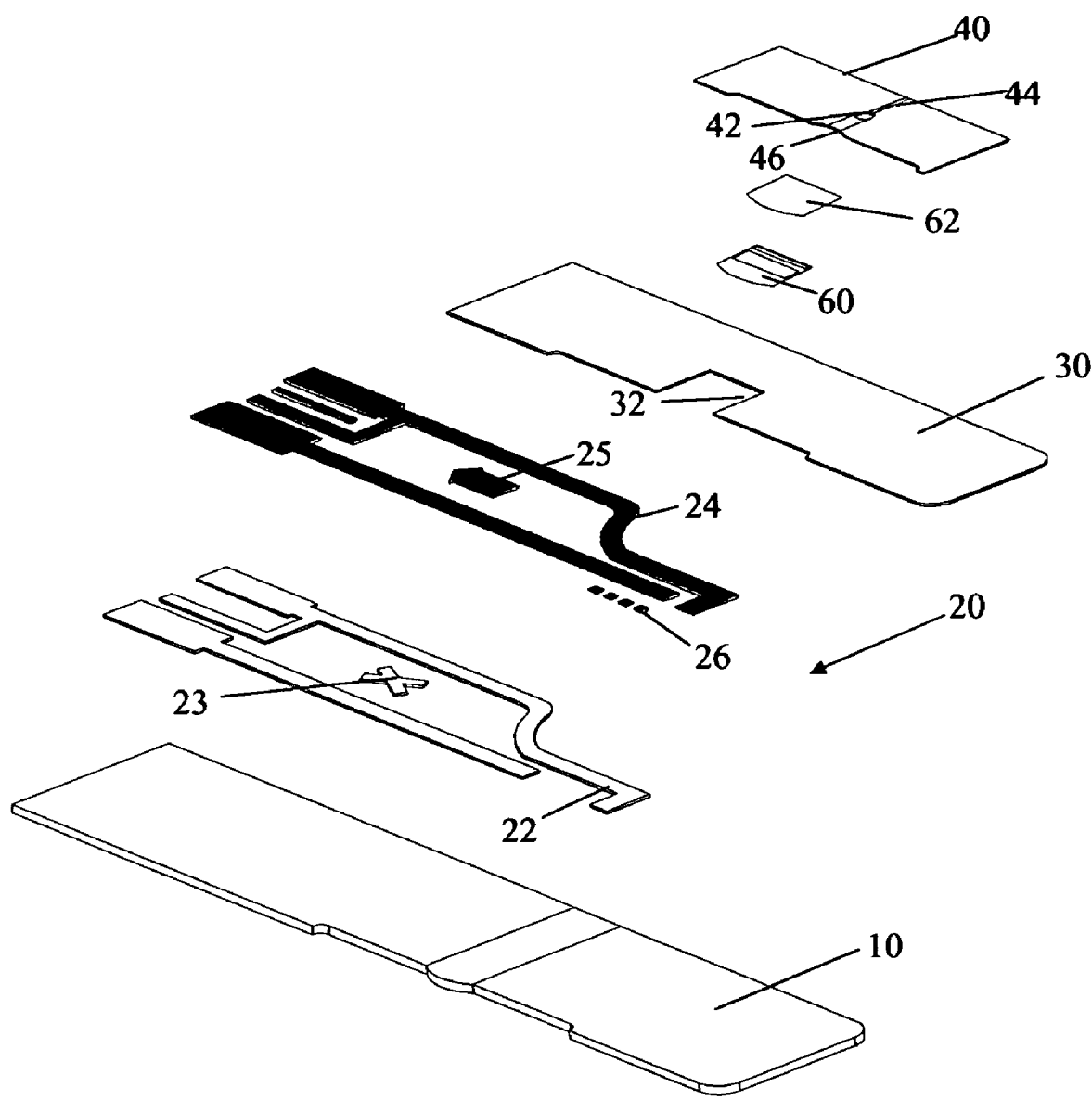
FIG. 4 is an exploded perspective view of a second embodiment of an electrochemical biosensor strip in accordance with the present invention.

With reference to FIG. 4, a second embodiment of the electrochemical biosensor strip in accordance with the present invention comprises a base (10), an electrode system (20), a spacer (30), a hydrophilic layer (60), a test reagent (62) and a cover (40), which structure is almost the same with the first embodiment of the electrochemical biosensor strip except that the cover (40) further has a hole (42) and a channel (44) and the spacer (30) does not has the exhausting channel. The hole (42) is formed corresponding to the opening (32) of the spacer (30). Preferably, the channel (44) opens to the opening (32) and communicates with the hole (42). The channel (44) and the hole (42) are both used to increase the flow rate of an analyte-containing fluid drawn into the opening (32).

Figure 5:
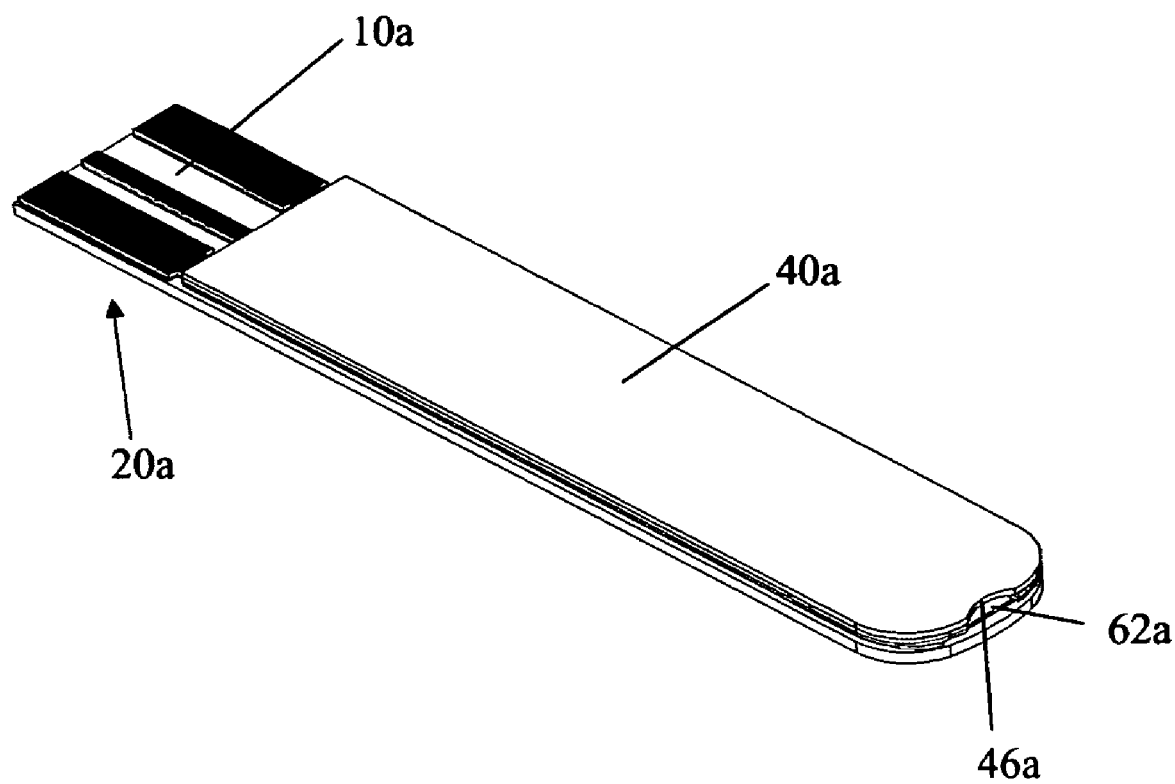
FIG. 5 is a perspective view of a third embodiment of an electrochemical biosensor strip in accordance with the present invention.
Figure 6:
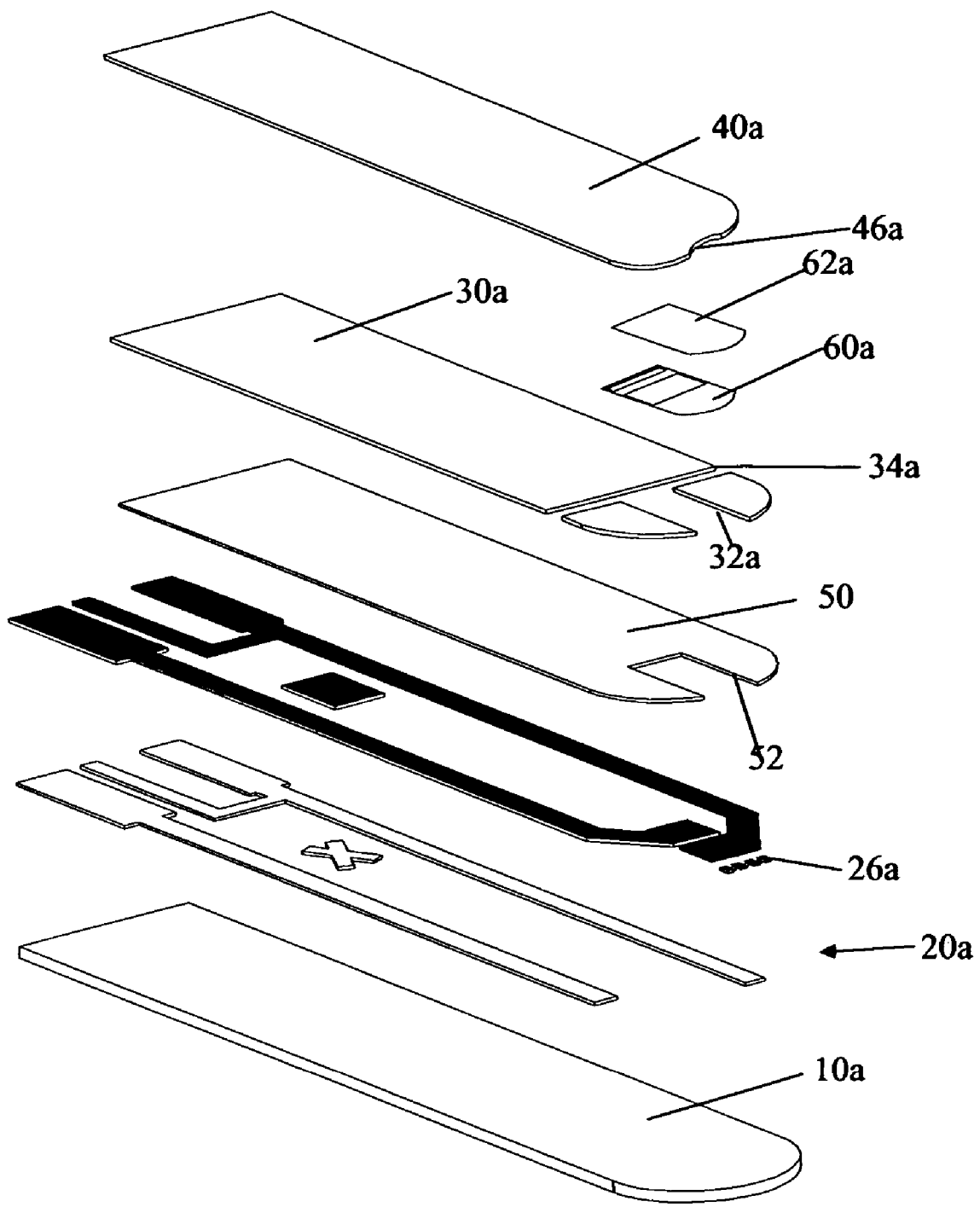
FIG. 6 is an exploded perspective view of the electrochemical biosensor strip in FIG. 5.

With reference to FIGS. 5 and 6, a third embodiment of the electrochemical biosensor strip in accordance with the present invention comprises a base (10a), an electrode system (20a), an insulating substance (50), a spacer (30a), a hydrophilic layer (60a), a test reagent (62a) and a cover (40a). The base (10a) may be rectangular and preferably is an insulating substance. The electrode system (20a) is laid on the base (10a) and preferably comprises two layers that are a silver layer and a carbon layer. The carbon layer and the silver layer respectively comprise at least three electrodes that respectively have a first end and a second end. The first ends of the electrodes are parallel and formed along a long edge of the strip. The second ends of the electrodes are defined corresponding to the test reagent (62a) and preferably are parallel with a short edge of the strip. The spacer (30a) is laid on the electrode system (20a). The electrodes will be exposed as the spacer (30a) is laid on the electrode system (20a) for electrical connection with a mating meter which measures some electrical property of an analyte-containing fluid after the analyte-containing fluid is mixed with the test reagent (62a) of the strip. Preferably, a rough unit (26a) formed on the base (10a) and more preferably the rough unit (26a) is formed on one end of the base (10a). In the drawing, the rough unit (26a) is parallel with one end of the electrode and near an outside of the base (10a) corresponding to the test reagent (62a). Preferably, the rough unit (26a) is formed adjacent to the electrode and more preferably is formed outside and parallel with the second ends of the electrodes.

The spacer (30a) comprises an opening (32a) formed in an end of the spacer (30a) and an exhausting channel (34a) defined communicating with the opening (32a). The opening (32a) exposes a predetermined portion of the electrode system (20a) for application of the test reagent (62a) to the exposed surface of electrode system (20a). Preferably, the opening (32a) and the exhausting channel (34a) is formed a T shape. The opening (32a) is used for introducing a sample into the strip. The insulating substance (50) is laid on the base (10a) and has an opening (52) formed corresponding to the opening (32a) of the spacer (30a). The test reagent (62a) is laid corresponding to the opening (52) of the insulating substance (50) and the opening (32a) of the spacer (30a). The electrode system (20a) has three electrodes and there is a short circuit between two electrodes of the three electrodes.

The hydrophilic layer (60a) is laid on the base (10a) corresponding to the opening (32a). Preferably, the hydrophilic layer (60a) is laid on an area of the base (10a) corresponding to the opening (32a) and excluding from the electrode system (20a) and laid on the electrode system (20a) about 50% to 0% of the electrode system (20a) corresponding to the opening (32a). More preferably, the hydrophilic layer (60a) is laid on the area of the base (32a) corresponding to the opening (32a) excluding from the electrode system (20a). On another aspect, the hydrophilic layer (60a) is laid on the area corresponding to the opening (32a) excluding from the working electrode and laid on the working electrode about 50% to 0% of the working electrode corresponding to the opening (32a). Preferably, the hydrophilic layer (60a) is laid on the area of the base (10a) corresponding to the opening (32a) and excluding from the working electrode.

The cover (40a) has a concave unit (46a) formed therein and corresponding to the opening (32a). The concave unit (46a) can increase receiving angles for drawing the analyte-containing fluid into the opening (32a) such that the analyte-containing fluid can be drawn into the opening (32a) more rapidly.

In accordance with the present invention, the electrochemical biosensor strip has a hydrophilic layer laid between the base and the test reagent so as to increase the binding effect and the stability of the test reagent on the base. In addition, since the hydrophilic layer laid on the electrode system will interfere with the signal transmission and let the signal decay so as to decrease the signal transmission and to decrease test accuracy. Further, if the hydrophilic layer is laid on the electrode system not equally, the test reagent will not uniformly spread on the electrode system. Therefore, the hydrophilic layer is laid on the area of the base corresponding to the test reagent excluding from the electrode system and laid on the electrode system about 50% to 0% of the electrode system corresponding to the test reagent. On the electrode system, a few part of the hydrophilic layer laid on the electrode system will let the test reagent spread out equally on the electrode system. It will also avoid the hydrophilic layer from interfering with the signal transmission.

For example, if the hydrophilic layer is laid on the working electrode completely, the signal will decay so as to decrease test accuracy. In general, the working electrode is laid about 30% of area that the base corresponding to the opening of the spacer and therefore, if the hydrophilic layer is laid on the base exception of the working electrode, the hydrophilic layer is laid about 70% of the area that the base corresponding to the opening of the spacer. That time, the signal produced by the reaction of the test reagent and the analyte-containing fluid will not be interfered because of the hydrophilic layer is not laid on the electrode system. If the hydrophilic layer is covered on the electrode system about 10% of the electrode system corresponding to the opening of the spacer, the hydrophilic layer is laid on the base about 73% of the area that the base corresponding to the opening of the spacer. It will not only increase the effect of the test reagent spreading on the electrode system but also decrease the noise signal to 90% so as to increase the intensity of the signal.

Furthermore, when the intensity of the signal is increasing, the amount of the test reagent, such as the amount of the enzyme, will decrease to achieve the same detecting efficiency so as to decrease manufacturing cost. Besides, the electrochemical biosensor strip is manufactured small nowadays so the area of the test reagent is small for decreasing needed amount of the analyte-containing fluid such that the signal is in relation to small. Because of the electrochemical biosensor strip of the present invention can approve to decrease noise and increase the intensity of the signal so as to increase test accuracy.

On the other hand, since the electrode system is laid on the base, the surface of the base for laying the test reagent is not a plane and showing concave areas that are the areas excluding from the electrode system. When the test reagent is directly laid on the base in this situation, it is difficult for the test reagent to spread on the base equally. The electrochemical biosensor strip of the present invention provides the hydrophilic layer laid on the base before the test reagent laid on the base so the hydrophilic layer may be full with the concave areas of the base corresponding to the test reagent and let the area of the base corresponding to the test reagent form a plane benefit for the test reagent spreading on the base equally. Therefore, the test reagent will bind on the base more stable so as to decrease the difference between each electrochemical biosensor strip and promote manufacturing quality.

Other embodiments of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. An electrochemical biosensor strip, comprising:
   a base;
   an electrode system laid on the base and a portion of the electrode system exposed for an electrical connection adapted to a meter and a predetermined portion of the electrode system exposed for applying a test reagent;
   a cover cooperating with the base to form a cavity for drawing an analyte-containing fluid therein to react with the test reagent; and
   a hydrophilic layer laid under the test reagent and laid on an area of the base excluded from the electrode system corresponding to the test reagent and also laid on the electrode system about 50% to 0% of the electrode system corresponding to the test reagent, wherein the hydrophilic layer has a size corresponding to the test reagent.

2. The electrochemical biosensor strip as claimed in claim 1, wherein the hydrophilic layer is water soluble cellulose, surfactant, thickening agent, organic polar compound or a combination thereof.

3. The electrochemical biosensor strip as claimed in claim 1, wherein the hydrophilic layer is methylcellulose, carboxymethyl cellulose, methylhydroxyethylcellulose, methylhydroxypropylcellulose, hydroxyethylcellulose, hydroxyethylcarboxymethylcellulose, carboxymethylhydroxyethylcellulose or a combination thereof.

4. The electrochemical biosensor strip as claimed in claim 1, wherein the electrode system comprises at least one working electrode and the hydrophilic layer laid both on an area of the base and the electrode system excluded from the working electrode corresponding to the test reagent and also laid on the working electrode about 50% to 0% of the working electrode corresponding to the test reagent.

5. The electrochemical biosensor strip as claimed in claim 4, wherein the hydrophilic layer laid on the working electrode is at least one strip-like shape.

6. The electrochemical biosensor strip as claimed in claim 5, wherein the hydrophilic layer laid on the working electrode is at least one strip-like shape formed on a middle of the working electrode.

7. The electrochemical biosensor strip as claimed in claim 4, wherein the hydrophilic layer laid on the area excluded from the working electrode is a plurality of strip-like shapes formed under the test reagent.

8. The electrochemical biosensor strip as claimed in claim 1, wherein the cover further comprises a concave unit formed corresponding to the test reagent and outside of the test reagent and the concave unit is semicircle-shape or semiellipse-shape.

9. The electrochemical biosensor strip as claimed in claim 1, further comprising a spacer covered on the electrode system to expose the portion of the electrode system for an electrical connection adapted to a meter, having an opening formed in one side of the spacer to expose the predetermined portion of the electrode system for applying the test reagent.

10. The electrochemical biosensor strip as claimed in claim 9, wherein the spacer further comprises an exhausting channel formed extendedly from the opening and opened to another side of the spacer.

11. The electrochemical biosensor strip as claimed in claim 9, wherein the cover further has a hole corresponding to the test reagent.

12. The electrochemical biosensor strip as claimed in claim 11, wherein the cover further has a channel formed corresponding to the opening of the spacer and communicating to the hole.

13. The electrochemical biosensor strip as claimed in claim 1, further comprising a spacer covered on the electrode system to expose the portion of the electrode system for an electrical connection adapted to a meter, having an opening formed in one end of the spacer to expose the predetermined portion of the electrode system for applying the test reagent.

14. The electrochemical biosensor strip as claimed in claim 13, wherein the spacer further has an exhausting channel communicated with the opening to form a T-shape.

15. The electrochemical biosensor strip as claimed in claim 14, further comprising an insulating substance laid on the electrode system which has an opening formed corresponding to the opening of the spacer.

16. The electrochemical biosensor strip as claimed in claim 1, further comprising a rough unit formed on the base corresponding to the test reagent and adjacent to the electrode system.

17. The electrochemical biosensor strip as claimed in claim 16, wherein the rough unit is a plurality of lines.

18. The electrochemical biosensor strip as claimed in claim 1, wherein the electrode system comprises at least three electrodes and a short circuit is formed between two selected electrodes of the at least three electrodes.

19. The electrochemical biosensor strip as claimed in claim 1, wherein the electrode system comprises a silver layer laid on the base and a carbon layer laid on the silver layer and the silver layer has a X-shaped unit formed on the base and between the electrodes and the carbon layer has an arrowhead shape unit formed corresponding to the X-shaped unit.

* * * * *

(12) EX PARTE REEXAMINATION CERTIFICATE (9711th)
United States Patent
Chen et al.

(10) Number: US 7,316,766 C1
(45) Certificate Issued: Jun. 24, 2013

(54) ELECTROCHEMICAL BIOSENSOR STRIP

(75) Inventors: Chun-Tung Chen, Taipei (TW); Tsai-Yun Lee, Sindian (TW); Shu-Mei Wu, Taipei (TW); Chia-Chi Wu, Kaohsiung (TW); Chun-Hui Pi, Yonghe (TW); Chao-Wang Chen, Taipei (TW)

(73) Assignee: Taidoc Technology Corporation, San-Chung, Taipei County (TW)

Reexamination Request:
No. 90/012,290, May 15, 2012

Reexamination Certificate for:
Patent No.: 7,316,766
Issued: Jan. 8, 2008
Appl. No.: 11/138,403
Filed: May 27, 2005

(51) Int. Cl.
*G01N 27/327* (2006.01)

(52) U.S. Cl.
USPC .............. 204/403.1; 204/403.02; 204/403.14

(58) Field of Classification Search
None
See application file for complete search history.

(56) References Cited

To view the complete listing of prior art documents cited during the proceeding for Reexamination Control Number 90/012,290, please refer to the USPTO's public Patent Application Information Retrieval (PAIR) system under the Display References tab.

*Primary Examiner* — Timothy J Kugel

(57) ABSTRACT

An electrochemical biosensor strip has a base, an electrode system, an optional spacer and a cover. The electrode system is laid on the base. The spacer is laid on the electrode system and exposes a portion of the electrode system for electrical connection with a meter and a different portion of the electrode system for application of a test reagent. The cover is covered on the spacer to form a cavity. Between the test reagent and the base, a hydrophilic layer is laid between them for increasing the binding effect of the test reagent on the base. The hydrophilic layer is laid on the area excluding from the electrode system and laid on the electrode system about 50% to 0% of the electrode system corresponding to the test reagent. The hydrophilic layer will not interfere with signal transmission of the electrode system so the test is more accurate.

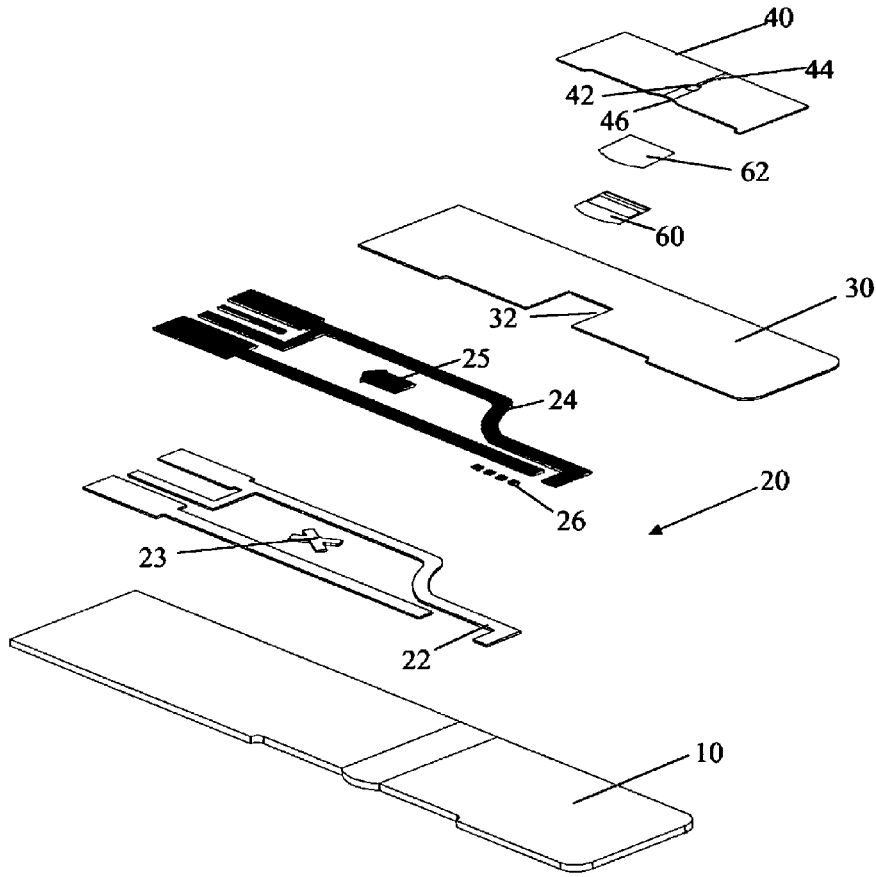

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 are determined to be patentable as amended.

Claims 2, 3 and 5-19, dependent on an amended claim, are determined to be patentable.

1. An electrochemical biosensor strip, comprising:
    a base;
    an electrode system laid on the base and a portion of the electrode system exposed for an electrical connection adapted to a meter and a predetermined portion of the electrode system exposed for applying a test reagent;
    a cover cooperating with the base to form a cavity for drawing an analyte-containing fluid therein to react with the test reagent; and
    a hydrophilic layer laid under the test reagent and laid on an area of the base excluded from the electrode system corresponding to the test reagent and also laid on *about 50% to 0% of the area of* the *predetermined portion of the* electrode system [about 50% to 0% of the electrode system corresponding to the test reagent] *exposed for applying the test reagent* wherein the hydrophilic layer has a size corresponding to the test reagent.

4. The electrochemical biosensor strip as claimed in claim 1, wherein the electrode system comprises at least one working electrode and the hydrophilic layer laid both on an area of the base and the electrode system excluded from the working electrode corresponding to the test reagent and also laid on *about 50% to 0% of the area of* the *predetermined portion of the* electrode system [about 50% to 0% of the electrode system corresponding to the test reagent] *exposed for applying the test reagent*.

* * * * *